(12) United States Patent
Iravani et al.

(10) Patent No.: US 10,391,610 B2
(45) Date of Patent: Aug. 27, 2019

(54) CORE CONFIGURATION FOR IN-SITU ELECTROMAGNETIC INDUCTION MONITORING SYSTEM

(71) Applicant: Applied Materials, Inc., Santa Clara, CA (US)

(72) Inventors: Hassan G. Iravani, Sunnyvale, CA (US); Kun Xu, Sunol, CA (US); Denis Ivanov, St. Petersburg (RU); Shih-Haur Shen, Sunnyvale, CA (US); Boguslaw A. Swedek, Cupertino, CA (US)

(73) Assignee: Applied Materials, Inc., Santa Clara, CA (US)

( * ) Notice: Subject to any disclaimer, the term of this patent is extended or adjusted under 35 U.S.C. 154(b) by 103 days.

(21) Appl. No.: 15/726,148

(22) Filed: Oct. 5, 2017

(65) Prior Publication Data
US 2018/0111251 A1  Apr. 26, 2018

Related U.S. Application Data

(60) Provisional application No. 62/411,407, filed on Oct. 21, 2016, provisional application No. 62/415,641, filed on Nov. 1, 2016.

(51) Int. Cl.
*B24B 49/04* (2006.01)
*B24B 49/10* (2006.01)
(Continued)

(52) U.S. Cl.
CPC .......... *B24B 49/045* (2013.01); *B24B 49/105* (2013.01); *G01N 27/025* (2013.01); *H01L 22/14* (2013.01); *H01L 22/26* (2013.01)

(58) Field of Classification Search
CPC .. B24B 49/045; B24B 49/105; G01N 27/025; H01L 22/14; H01L 22/26
(Continued)

(56) References Cited

U.S. PATENT DOCUMENTS

| 4,000,458 A | * | 12/1976 | Miller | G01N 27/023 324/236 |
| 6,159,073 A | * | 12/2000 | Wiswesser | B24B 37/04 451/288 |

(Continued)

FOREIGN PATENT DOCUMENTS

KR  10-1105264  1/2012

OTHER PUBLICATIONS

International Search Report and Written Opinion in International Application No. PCT/US2017/055377, dated Jan. 17, 2018, 13 pages.

*Primary Examiner* — George B Nguyen
(74) *Attorney, Agent, or Firm* — Fish & Richardson P.C.

(57) ABSTRACT

An apparatus for chemical mechanical polishing includes a support for a polishing pad having a polishing surface, and an electromagnetic induction monitoring system to generate a magnetic field to monitor a substrate being polished by the polishing pad. The electromagnetic induction monitoring system includes a core and a coil wound around a portion of the core. The core includes a back portion, a center post extending from the back portion in a first direction normal to the polishing surface, and an annular rim extending from the back portion in parallel with the center post and surrounding and spaced apart from the center post by a gap. A width of the gap is less than a width of the center post, and a surface area of a top surface of the annular rim is at least two times greater than a surface area of a top surface of the center post.

20 Claims, 5 Drawing Sheets

(51) Int. Cl.
*G01N 27/02* (2006.01)
*H01L 21/66* (2006.01)

(58) Field of Classification Search
USPC .............................................. 451/8
See application file for complete search history.

(56) References Cited

U.S. PATENT DOCUMENTS

| | | | | |
|---|---|---|---|---|
| 7,001,242 | B2* | 2/2006 | Birang | B24B 37/013 |
| | | | | 451/11 |
| 7,654,888 | B2* | 2/2010 | Zuniga | B24B 37/30 |
| | | | | 451/288 |
| 9,023,667 | B2* | 5/2015 | Iravani | H01L 22/14 |
| | | | | 438/10 |
| 2002/0055192 | A1* | 5/2002 | Redeker | B24B 37/013 |
| | | | | 438/8 |
| 2008/0064301 | A1 | 3/2008 | Birang et al. | |
| 2011/0189925 | A1 | 8/2011 | Iravani et al. | |
| 2012/0088438 | A1 | 4/2012 | Tada et al. | |
| 2012/0276661 | A1 | 11/2012 | Iravani et al. | |

\* cited by examiner

CORE CONFIGURATION FOR IN-SITU ELECTROMAGNETIC INDUCTION MONITORING SYSTEM

CROSS-REFERENCE TO RELATED APPLICATIONS

This application claims priority to U.S. Provisional Application Ser. No. 62/411,407, filed on Oct. 21, 2016, and claims priority to U.S. Provisional Application Ser. No. 62/415,641, filed on Nov. 1, 2016, each of which is incorporated by reference.

TECHNICAL FIELD

The present disclosure relates to electromagnetic induction monitoring, e.g., eddy current monitoring, during processing of a substrate.

BACKGROUND

An integrated circuit is typically formed on a substrate (e.g. a semiconductor wafer) by the sequential deposition of conductive, semiconductive or insulative layers on a silicon wafer, and by the subsequent processing of the layers.

One fabrication step involves depositing a filler layer over a non-planar surface, and planarizing the filler layer until the non-planar surface is exposed. For example, a conductive filler layer can be deposited on a patterned insulative layer to fill the trenches or holes in the insulative layer. The filler layer is then polished until the raised pattern of the insulative layer is exposed. After planarization, the portions of the conductive layer remaining between the raised pattern of the insulative layer form vias, plugs and lines that provide conductive paths between thin film circuits on the substrate. In addition, planarization may be used to planarize the substrate surface for lithography.

Chemical mechanical polishing (CMP) is one accepted method of planarization. This planarization method typically requires that the substrate be mounted on a carrier head. The exposed surface of the substrate is placed against a rotating polishing pad. The carrier head provides a controllable load on the substrate to push it against the polishing pad. A polishing liquid, such as slurry with abrasive particles, is supplied to the surface of the polishing pad.

During semiconductor processing, it may be important to determine one or more characteristics of the substrate or layers on the substrate. For example, it may be important to know the thickness of a conductive layer during a CMP process, so that the process may be terminated at the correct time. A number of methods may be used to determine substrate characteristics. For example, optical sensors may be used for in-situ monitoring of a substrate during chemical mechanical polishing. Alternately (or in addition), an eddy current sensing system may be used to induce eddy currents in a conductive region on the substrate to determine parameters such as the local thickness of the conductive region.

SUMMARY

In one aspect, an apparatus for chemical mechanical polishing includes a support for a polishing pad having a polishing surface, and an electromagnetic induction monitoring system to generate a magnetic field to monitor a substrate being polished by the polishing pad. The electromagnetic induction monitoring system includes a core and a coil wound around a portion of the core. The core includes a back portion, a center post extending from the back portion in a first direction normal to the polishing surface, and an annular rim extending from the back portion in parallel with the center post and surrounding and spaced apart from the center post by a gap. The center post has a first width in a second direction parallel to the polishing surface, the annular rim has a second width in the second direction and the gap has a third width in the second direction. The third width is less than the first width, and a surface area of a top surface of the annular rim is at least two times greater than a surface area of a top surface of the center post.

Implementations may include one or more of the following features.

The second width may be greater than the first width. The second width may be 1.1 to 1.5 times greater than the first width. The third width may be 50% to 75% of the first width. The surface area of the top surface of the annular rim may be at least three times greater than the surface area of the top surface of the center post. A height of the center post may be equal to a height of the annular rim portion. The third width may be between about 30% and 70% of the second width. The coil and core may be configured to provide a resonant frequency of at least 12 MHz, e.g., between about 14 and 16 MHz. The core may be nickel zinc ferrite.

In another aspect, an apparatus for chemical mechanical polishing includes a support for a polishing pad having a polishing surface, and an electromagnetic induction monitoring system to generate a magnetic field to monitor a substrate being polished by the polishing pad. The electromagnetic induction monitoring system includes a core and a winding assembly. The core includes a back portion, a center post extending from the back portion in a first direction normal to the surface of the platen, and an annular rim extending from the back portion in parallel with the center post and surrounding and spaced apart from the center post by a gap. The center post has a first width in a second direction parallel to the surface of the platen, the annular rim has a second width in the second direction, and the gap has a third width in the second direction. The winding assembly is a cylindrical body fitting in the gap. The winding assembly includes a coil wound around the center post, and the winding assembly has a fourth width between an inner diameter and an outer diameter of the cylindrical body. The fourth width is at least 80% of the third width.

Implementations may include one or more of the following features.

The winding assembly may include a bobbin, the coil may be wound around the bobbin, and an inner surface of the bobbin may provide the inner diameter of the winding assembly. The inner surface of the bobbin may contact an outer surface of the center post. The winding assembly may include a tape contacting and surrounding the coil, and an outer surface of the tape may provide the outer diameter of the winding assembly. The outer surface of the tape may contact an inner surface of the annular rim.

The coil may have no more than two winding layers around the center post, e.g., the coil may have a single winding layer around the center post. The fourth width may be at least 90% of the third width. The third width may be about 1 to 2 mm. The third width may be less than the first width, and a surface area of a top surface of the annular rim may be at least two times greater than a surface area of a top surface of the center post.

Certain implementations can include one or more of the following advantages. Spatial resolution of the eddy current sensor can be improved. The eddy current sensor can be configured for monitoring of conductive features that have a high impedance, e.g., metal sheets formed of a low conductance metal such as titanium or cobalt, metal residue, or metal lines.

The details of one or more implementations are set forth in the accompanying drawings and the description below. Other aspects, features and advantages will be apparent from the description and drawings, and from the claims.

BRIEF DESCRIPTION OF DRAWINGS

Like reference symbols in the various drawings indicate like elements.

DETAILED DESCRIPTION

A CMP system can use an eddy current monitoring systems to detect a thickness of a metal layer on a substrate during polishing. During polishing of the metal layer, the eddy current monitoring system can determine the thickness of the metal layer in different regions of the substrate. The thickness measurements can be used to detect the polishing endpoint or to adjust processing parameters of the polishing process in real time to reduce polishing non-uniformity.

One issue with eddy current monitoring is that the eddy current is induced in the conductive layer in a region whose size depends on the spread of the magnetic field; the greater the spread of the magnetic field, the lower the resolution of the eddy current monitoring system. With ever increasing demands of integrated circuit fabrication, there is a need for increased spatial resolution of the eddy current sensor, e.g., in order to provide improved control of the polishing parameters. Appropriate selection of the physical configuration of the magnetic core can reduce the spread of the magnetic field and provide improved resolution.

Figure 1:
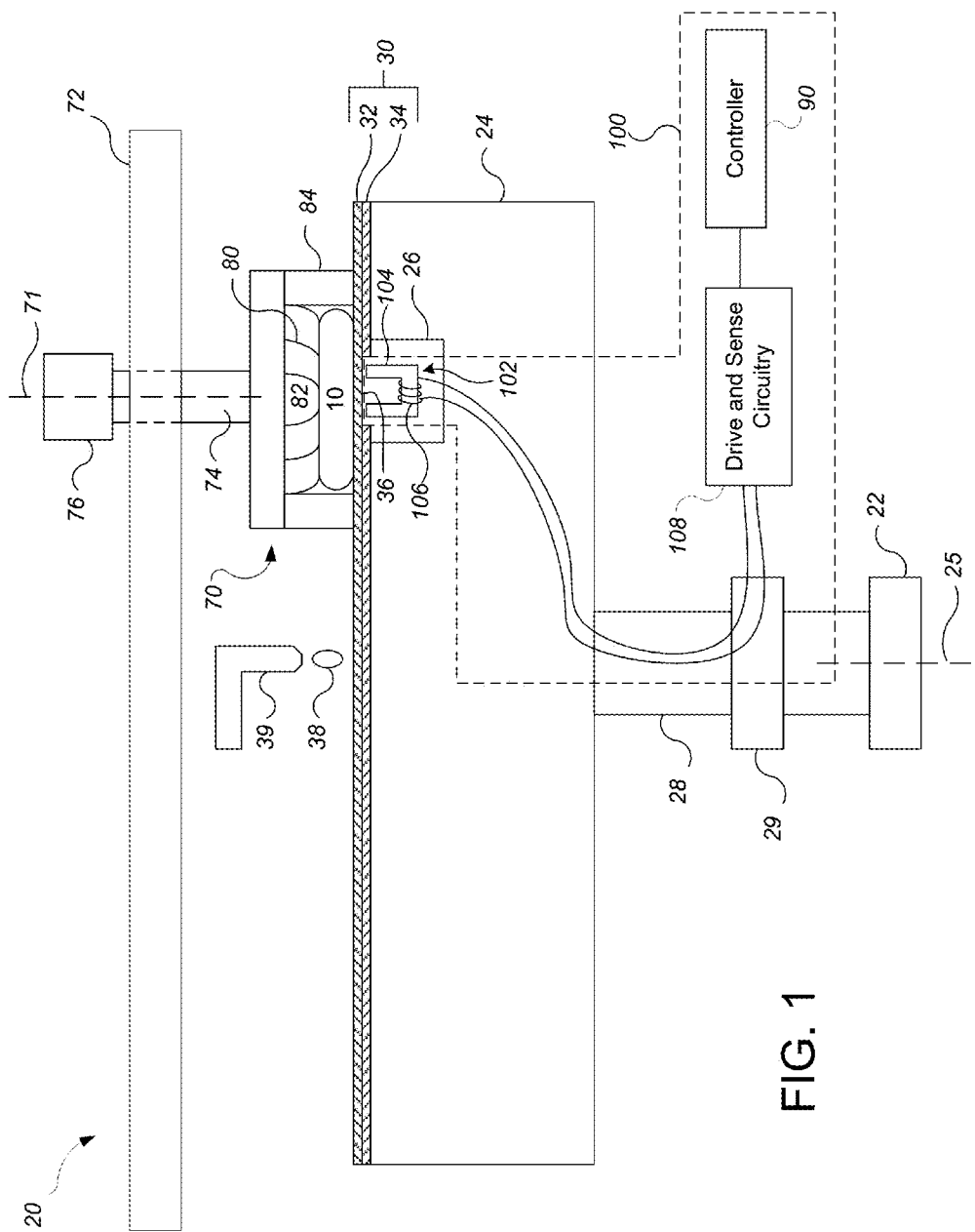
FIG. 1 is a schematic side view, partially cross-sectional, of a chemical mechanical polishing station that includes an electromagnetic induction monitoring system.
Figure 2:
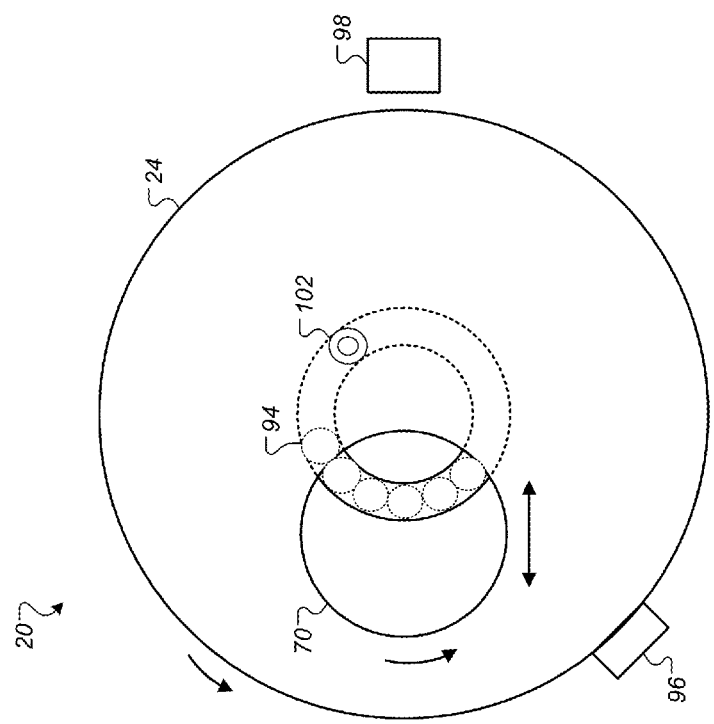
FIG. 2 is a schematic top view of the chemical mechanical polishing station of FIG. 1.

FIGS. 1 and 2 illustrate an example of a polishing station 20 of a chemical mechanical polishing apparatus. The polishing station 20 includes a rotatable disk-shaped platen 24 on which a polishing pad 30 is situated. The platen 24 is operable to rotate about an axis 25. For example, a motor 22 can turn a drive shaft 28 to rotate the platen 24. The polishing pad 30 can be a two-layer polishing pad with an outer polishing layer 34 and a softer backing layer 32.

The polishing station 22 can include a supply port or a combined supply-rinse arm 39 to dispense a polishing liquid 38, such as slurry, onto the polishing pad 30. The polishing station 22 can include a pad conditioner apparatus with a conditioning disk to maintain the surface roughness of the polishing pad.

The carrier head 70 is operable to hold a substrate 10 against the polishing pad 30. The carrier head 70 is suspended from a support structure 72, e.g., a carousel or a track, and is connected by a drive shaft 74 to a carrier head rotation motor 76 so that the carrier head can rotate about an axis 71. Optionally, the carrier head 70 can oscillate laterally, e.g., on sliders on the carousel or track 72; or by rotational oscillation of the carousel itself.

In operation, the platen is rotated about its central axis 25, and the carrier head is rotated about its central axis 71 and translated laterally across the top surface of the polishing pad 30. Where there are multiple carrier heads, each carrier head 70 can have independent control of its polishing parameters, for example each carrier head can independently control the pressure applied to each respective substrate.

The carrier head 70 can include a flexible membrane 80 having a substrate mounting surface to contact the back side of the substrate 10, and a plurality of pressurizable chambers 82 to apply different pressures to different zones, e.g., different radial zones, on the substrate 10. The carrier head can also include a retaining ring 84 to hold the substrate.

A recess 26 is formed in the platen 24, and optionally a thin section 36 can be formed in the polishing pad 30 overlying the recess 26. The recess 26 and thin pad section 36 can be positioned such that regardless of the translational position of the carrier head they pass beneath substrate 10 during a portion of the platen rotation. Assuming that the polishing pad 30 is a two-layer pad, the thin pad section 36 can be constructed by removing a portion of the backing layer 32, and optionally by forming a recess in the bottom of the polishing layer 34. The thin section can optionally be optically transmissive, e.g., if an in-situ optical monitoring system is integrated into the platen 24.

Figure 3A:
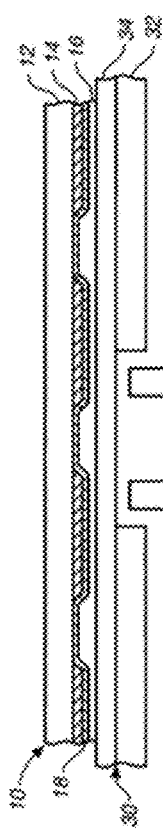
FIGS. 3A-3C are schematic cross-sectional side views illustrating a method of polishing a substrate.

Referring to FIG. 3A, the polishing system 20 can be used to polish a substrate 10 that includes a conductive material overlying and/or inlaid in a patterned dielectric layer. For example, the substrate 10 can include a layer of conductive material 16, e.g., a metal, e.g., copper, aluminum, cobalt or titanium, that overlies and fills trenches in a dielectric layer 14, e.g., silicon oxide or a high-k dielectric. Optionally a barrier layer 18, e.g., tantalum or tantalum nitride, can line the trenches and separate the conductive material 16 from the dielectric layer 14. The conductive material 16 in the trenches can provide vias, pads and/or interconnects in a completed integrated circuit. Although the dielectric layer 14 is illustrated as deposited directly on a semiconductor wafer 12, one or more other layers can be interposed between the dielectric layer 14 and the wafer 12.

Figure 3B:
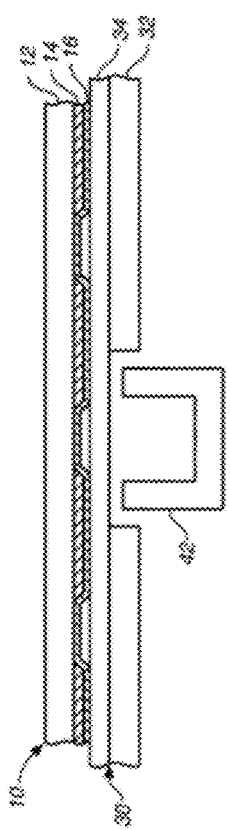
Figure 3C:
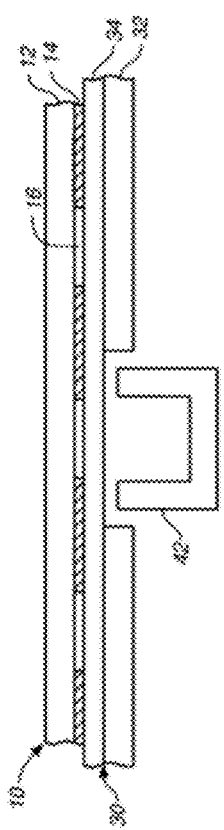

Initially, the conductive material 16 overlies the entire dielectric layer 14. As polishing progresses, the bulk of the conductive material 16 is removed, exposing the barrier layer 18 (see FIG. 3B). Continued polishing then exposes the patterned top surface of the dielectric layer 14 (see FIG. 3C). Additional polishing can then be used to control the depth of the trenches that contain the conductive material 16.

Returning to FIG. 1, the polishing system 20 includes an in-situ electromagnetic induction monitoring system 100 which can be coupled to or be considered to include a controller 90. A rotary coupler 29 can be used to electrically connect components in the rotatable platen 24, e.g., the sensors of the in-situ monitoring systems, to components outside the platen, e.g., drive and sense circuitry or the controller 90.

The in-situ electromagnetic induction monitoring system 100 is configured to generate a signal that depends on a depth of the conductive material 16, e.g., the metal. The electromagnetic induction monitoring system can operate either by generation of eddy-currents in the conductive material, which can be either the sheet of conductive material that overlies the dielectric layer or the conductive material remaining in trenches after the dielectric layer is exposed, or generation of current in a conductive loop formed in a trench in the dielectric layer on the substrate.

In operation, the polishing system 20 can use the in-situ monitoring system 100 to determine when the conductive layer has reached a target thickness, e.g., a target depth for metal in a trench or a target thickness for a metal layer overlying the dielectric layer, and then halts polishing. Alternatively or in addition, the polishing system 20 can use the in-situ monitoring system 100 to determine differences in thickness of the conductive material 16 across the substrate 10, and uses this information to adjust the pressure in one or more chambers 82 in the carrier head 80 during polishing in order to reduce polishing non-uniformity.

The in-situ monitoring system 100 can include a sensor 102 installed in a recess 26 in the platen 24. The sensor 102 can include a magnetic core 104 positioned at least partially in the recess 26, and at least one coil 106 wound around a portion of the core 104. Drive and sense circuitry 108 is electrically connected to the coil 106. The drive and sense circuitry 108 generates a signal that can be sent to the controller 90. Although illustrated as outside the platen 24, some or all of the drive and sense circuitry 108 can be installed in the platen 24.

Referring to FIG. 2, as the platen 24 rotates, the sensor 102 sweeps below the substrate 10. By sampling the signal from the circuitry 108 at a particular frequency, the circuitry 108 generates measurements at a sequence of sampling zones 94 across the substrate 10. For each sweep, measurements at one or more of the sampling zones 94 can be selected or combined. Thus, over multiple sweeps, the selected or combined measurements provide the time-varying sequence of values.

The polishing station 20 can also include a position sensor 96, such as an optical interrupter, to sense when the sensor 102 is underneath the substrate 10 and when the sensor 102 is off the substrate. For example, the position sensor 96 can be mounted at a fixed location opposite the carrier head 70. A flag 98 can be attached to the periphery of the platen 24. The point of attachment and length of the flag 98 is selected so that it can signal the position sensor 96 when the sensor 102 sweeps underneath the substrate 10.

Alternately or in addition, the polishing station 20 can include an encoder to determine the angular position of the platen 24.

Returning to FIG. 1, a controller 90, e.g., a general purpose programmable digital computer, receives the signals from the in-situ monitoring system 100. Since the sensor 102 sweeps beneath the substrate 10 with each rotation of the platen 24, information on the depth of the conductive layer, e.g., the bulk layer or conductive material in the trenches, is accumulated in-situ (once per platen rotation). The controller 90 can be programmed to sample measurements from the in-situ monitoring system 100 when the substrate 10 generally overlies the sensor 102.

In addition, the controller 90 can be programmed to calculate the radial position of each measurement, and to sort the measurements into radial ranges.

Figure 4:
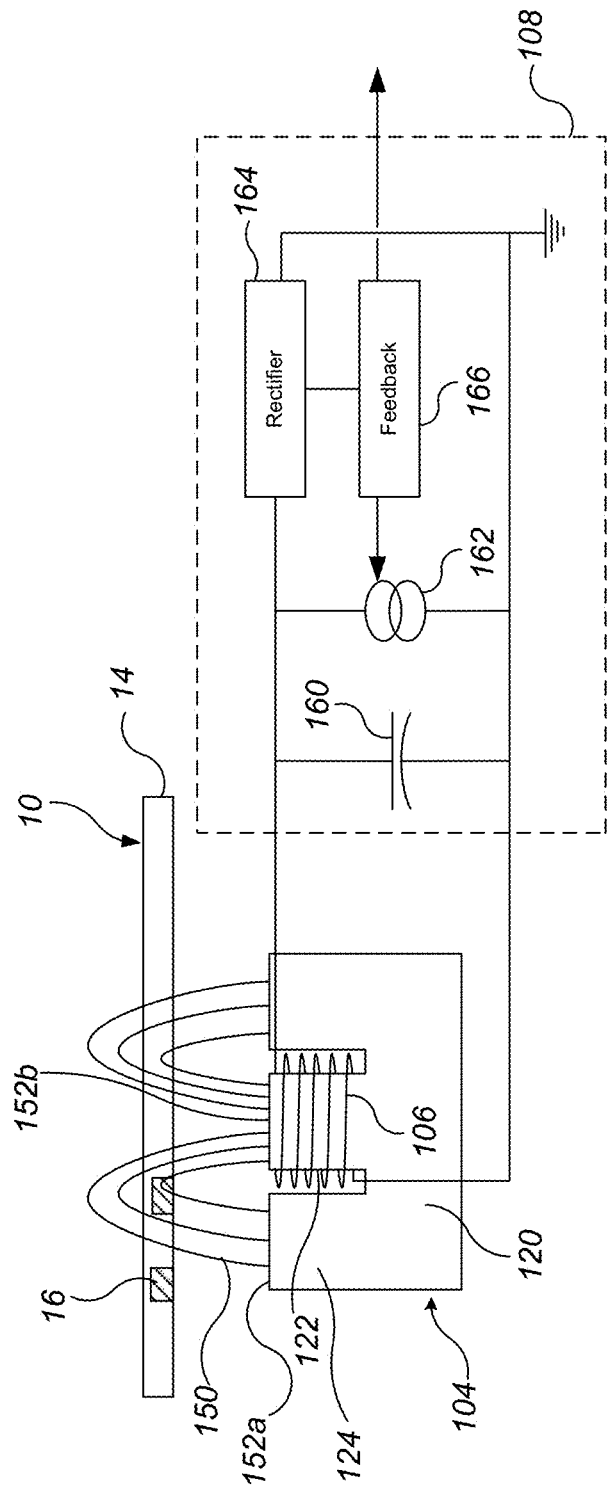
FIG. 4 is a schematic circuit diagram of a drive system for an electromagnetic induction monitoring system.
Figures 5A, 5B:
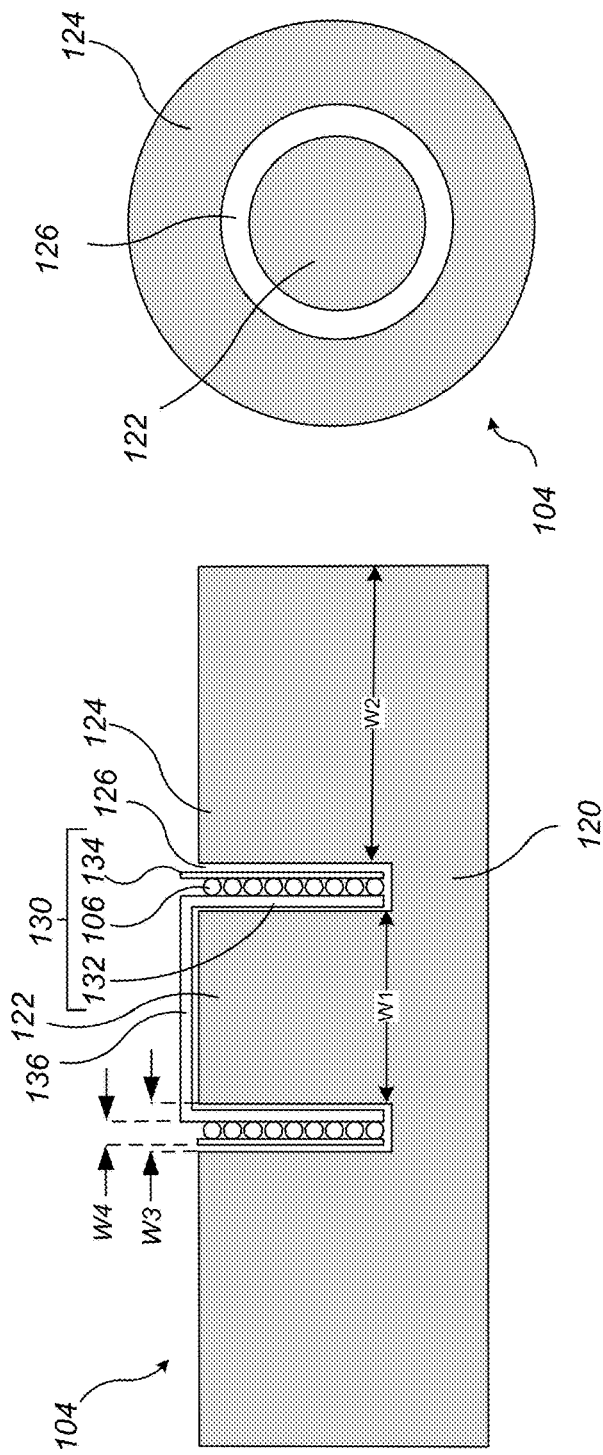
FIGS. 5A and 5B are schematic top and side views of the core of the electromagnetic induction monitoring system.

FIG. 4 illustrates an example of the drive and sense circuitry 108. The circuitry 108 applies an AC current to the coil 106, which generates a magnetic field 150 between two poles 152a and 152b of the core 104. In operation, when the substrate 10 intermittently overlies the sensor 104, a portion of the magnetic field 150 extends into the substrate 10.

The circuitry 108 can include a capacitor 160 connected in parallel with the coil 106. Together the coil 106 and the capacitor 160 can form an LC resonant tank. In operation, a current generator 162 (e.g., a current generator based on a marginal oscillator circuit) drives the system at the resonant frequency of the LC tank circuit formed by the coil 106 (with inductance L) and the capacitor 160 (with capacitance C). The current generator 162 can be designed to maintain the peak to peak amplitude of the sinusoidal oscillation at a constant value. A time-dependent voltage with amplitude V0 is rectified using a rectifier 164 and provided to a feedback circuit 166. The feedback circuit 166 determines a drive current for current generator 162 to keep the amplitude of the voltage V0 constant. Marginal oscillator circuits and feedback circuits are further described in U.S. Pat. Nos. 4,000,458, and 7,112,960.

As an eddy current monitoring system, the electromagnetic induction monitoring system 100 can be used to monitor the thickness of a conductive layer by inducing eddy currents in the conductive sheet, or to monitor the depth of a conductive material in a trench by inducing eddy currents in the conductive material. Alternatively, as an inductive monitoring system, the electromagnetic induction monitoring system can operate by inductively generating a current in a conductive loop formed in the dielectric layer 14 of the substrate 10 for the purpose of monitoring, e.g., as described in U.S. Patent Publication No. 2015-0371907.

If monitoring of the thickness of a conductive layer on the substrate is desired, then when the magnetic field 150 reaches the conductive layer, the magnetic field 150 can pass through and generate a current (if the target is a loop) or create an eddy-current (if the target is a sheet). This creates an effective impedance, thus increasing the drive current required for the current generator 162 to keep the amplitude of the voltage V0 constant. The magnitude of the effective impedance depends on the thickness of the conductive layer. Thus, the drive current generated by the current generator 162 provides a measurement of the thickness of the conductive layer being polished.

Other configurations are possible for the drive and sense circuitry 108. For example, separate drive and sense coils could be wound around the core, the drive coil could be driven at a constant frequency, and the amplitude or phase (relative to the driving oscillator) of the current from the sense coil could be used for the signal.

FIGS. 4A and 4B illustrate an example of a core 104 for the in-situ monitoring system 100. The core 104 has a body formed of a non-conductive material with a relatively high magnetic permeability (e.g., $\mu$ of about 2500 or more). Specifically, the core 104 can be nickel-zinc ferrite or magnesium-zinc ferrite.

In some implementations, the core 104 is coated with a protective layer. For example, the core 104 can be coated with a material such as parylene to prevent water from entering pores in the core 104, and to prevent coil shorting.

The core 104 can be round core, also known as a pot core. The core 104 includes a back portion 120, a center post 122 that extends from the back portion 120, and an annular rim 124 surrounding and spaced apart from the center post 122 by a gap 126 and also extending from the back portion 120. The annular rim 124 can be spaced apart from the center post 122 by a uniform distance around the perimeter of the center post 122. The annular rim 124 can completely enclose the center post 122 (as seen in the top view of FIG. 4B).

A winding assembly 130 fits into the gap 126. The winding assembly can a cylindrical body. The winding assembly has a width (W4), which can be the distance between an inner diameter and an outer diameter of the cylindrical body.

The winding assembly 130 includes at least the coil 106, which is wound around the center post 122 of the core 104, e.g., only around the center post 122. In order to reduce the required width of the gap 126, the coil 106 can have just one or two layers of windings.

The winding assembly 130 can also include a bobbin 132. The bobbin 132 fits around the center post 122, and the coil 106 is wound around the bobbin 132. The bobbin 132 can also include a cap 136 that rests against the top surface of the post 124 to set the vertical position of the coil portion. This permits easier assembly of the sensor 102. The bobbin can be a dielectric material, e.g., a plastic. The inner surface of the bobbin 132 can provide the outer diameter of the winding assembly.

The winding assembly 130 can also include a tape 134 that covers the outer surface of the coil 106, e.g., to protect the coil 106. The outer surface of the tape 134 can provide the inner diameter of the winding assembly.

The back portion 120 of the core 106 can be a generally planar body and can have a top face parallel to the top surface of the platen, e.g., parallel to the substrate and the polishing pad during the polishing operation. The back portion 120 can have a height (H) that is measured normal to the top surface of the platen. The center post 122 and the annular rim 124 extend from the back portion 120 in a direction normal to a top surface of the back portion 120 and extend in parallel with each other. The center post 122 and the annular rim 124 can have the same height.

In some implementations, the core 104 is generally circular. For example, the back portion 120 can be disk-shaped, the center post 122 can be circular, and the annular rim 124 can similarly be ring-shaped. However, other configurations are possible that maintain an annular configuration for the rim 124, e.g., the center post 122 could be a square and the rim 124 could similarly trace the perimeter of a square.

The center post 122 has a width (W1) and the annular rim 124 has a width (W2), each of which can be measured along a direction parallel to the top surface of the platen, e.g., parallel to the faces of the substrate and polishing pad during the polishing operation, and are substantially linear and extend in parallel to each other. The width W1 of the center post 122 can be substantially the minimum possible while providing the necessary magnetic flux for a clear signal.

The annular rim 124 is separated from the center post 122 by a gap having a width (W3). The width of the gap 126 can be substantially the minimum possible while providing room for the winding assembly 130 to fit in the gap 126. For example, the width (W4) of the winding can be at least 80%, e.g., about 90%, of the width of the gap 126. This maintains the magnetic field in a region close to the center post 122, and increases spatial resolution. In some implementations, the outer surface of the winding assembly 130 contacts the inner surface of the annular rim 124.

The widths W1, W2 and W3 can be selected such that the surface area of the annular rim 124 is larger, e.g., at least two times larger, e.g., at least three times larger, e.g., at least four times larger, than the surface area of the center post 122. This permits more flux lines to be collected and pushed toward the inner diameter of the annular rim 124, thereby further improving the spatial resolution.

For center post having a larger width, e.g., where W1 is 3 mm or larger, the surface area of the annular rim 124 can be at least two times, e.g., two to three times, larger than the surface area of the center post 122. For this case, the width W3 can be up to 1 mm. For center post having a larger width, e.g., where W1 is less than 3 mm, the surface area of the annular rim 124 can be at least four times, e.g., four to six times, larger than the surface area of the center post 122. For this case, the width W3 can be up to 2 mm.

The annular rim 124 can have a width W2 that is larger than the half the width W1 (e.g., larger than the radius) of the center post 122. In some implementations, the annular rim 124 has a width W2 that is larger than the width W1 (e.g., larger than the diameter) of the center post 122, e.g., at least 10% larger. For example, the center post 122 can have a width of 1.5 mm, the gap 126 can have a width of about 1 mm, and the annular rim 124 can have a width of about 1.75 mm.

The center post 122 and the annular rim 124 have a height Hp, which is the distance that the they extend from the back portion 120 of the core 104. The height Hp can be greater than the widths W1 and W2. In some implementations, the height Hp is the same as the distances W3 separating the prongs 504a-c.

In general, the in-situ eddy current monitoring system 400 is constructed with a resonant frequency of about 50 kHz to 50 MHz. For example, for the eddy current monitoring system 400 shown in FIG. 4A, the coil 422 can have an inductance of about 0.1 to 50 microH, e.g., 0.75 uH, and the capacitor 424 can have a capacitance of about 40 pF to about 0.022 uF, e.g., 150 pF.

The electromagnetic induction monitoring system can be used in a variety of polishing systems. Either the polishing pad, or the carrier head, or both can move to provide relative motion between the polishing surface and the substrate. The polishing pad can be a circular (or some other shape) pad secured to the platen, a tape extending between supply and take-up rollers, or a continuous belt. The polishing pad can be affixed on a platen, incrementally advanced over a platen between polishing operations, or driven continuously over the platen during polishing. The pad can be secured to the platen during polishing, or there can be a fluid bearing between the platen and polishing pad during polishing. The polishing pad can be a standard (e.g., polyurethane with or without fillers) rough pad, a soft pad, or a fixed-abrasive pad.

In addition, although the description above has focused on polishing, the core design can be applicable to in-situ monitoring during other substrate processing tools and steps that modify the thickness of the layer on the substrate, e.g., etching or deposition, and to in-line or stand-alone system measurements.

A number of embodiments of the invention have been described. Nevertheless, it will be understood that various modifications may be made without departing from the spirit and scope of the invention. Accordingly, other embodiments are within the scope of the following claims.

What is claimed is:

1. An apparatus for chemical mechanical polishing, comprising:
    a support for a polishing pad having a polishing surface; and
    an electromagnetic induction monitoring system to generate a magnetic field to monitor a substrate being polished by the polishing pad, the electromagnetic induction monitoring system comprising a core and a coil wound around a portion of the core, the core including
        a back portion,
        a center post extending from the back portion in a first direction normal to the polishing surface, the center post having a first width in a second direction parallel to the polishing surface, and
        an annular rim extending from the back portion in parallel with the center post and surrounding and spaced apart from the center post by a gap, the annular rim having a second width in the second direction and the gap having a third width in the second direction, wherein the third width is less than the first width, and a surface area of a top surface of the annular rim is at least two times greater than a surface area of a top surface of the center post.

2. The apparatus of claim 1, wherein the second width is greater than the first width.

3. The apparatus of claim 2, wherein the second width is 1.1 to 1.5 times greater than the first width.

4. The apparatus of claim 1, wherein the third width is 50% to 75% of the first width.

5. The apparatus of claim 1, wherein the surface area of the top surface of the annular rim is at least three times greater than the surface area of the top surface of the center post.

6. The apparatus of claim 1, wherein a height of the center post is equal to a height of the annular rim.

7. The apparatus of claim 1, wherein the third width is between about 30% and 70% of the second width.

8. The apparatus of claim 1, wherein the coil and core are configured to provide a resonant frequency of 50 kHz to 50 MHz.

9. The apparatus of claim 8, wherein the coil and core are configured to provide a resonant frequency between about 14 and 16 MHz.

10. The apparatus of claim 1, wherein the core is nickel zinc ferrite or magnesium zinc ferrite.

11. An apparatus for chemical mechanical polishing, comprising:
a support for a polishing pad having a polishing surface; and
an electromagnetic induction monitoring system to generate a magnetic field to monitor a substrate being polished by the polishing pad, the electromagnetic induction monitoring system comprising a core and a winding assembly,
wherein the core includes
a back portion,
a center post extending from the back portion in a first direction normal to the polishing surface, the center post having a first width in a second direction parallel to the polishing surface, and
an annular rim extending from the back portion in parallel with the center post and surrounding the center post and spaced apart from the center post by a gap, the annular rim having a second width in the second direction and the gap having a third width in the second direction,
and wherein the winding assembly is a cylindrical body fitting in the gap, the winding assembly includes a coil wound around the center post, the winding assembly has a fourth width between an inner diameter and an outer diameter of the cylindrical body, and wherein the fourth width is at least 80% of the third width.

12. The apparatus of claim 11, wherein the winding assembly includes a bobbin, the coil is wound around the bobbin, and an inner surface of the bobbin provides the inner diameter of the winding assembly.

13. The apparatus of claim 12, wherein the inner surface of the bobbin contacts an outer surface of the center post.

14. The apparatus of claim 11, wherein the winding assembly includes a tape contacting and surrounding the coil, and an outer surface of the tape provides the outer diameter of the winding assembly.

15. The apparatus of claim 14, wherein the outer surface of the tape contacts an inner surface of the annular rim.

16. The apparatus of claim 11, wherein the coil comprises no more than two winding layers around the center post.

17. The apparatus of claim 14, wherein the coil comprises a single winding layer around the center post.

18. The apparatus of claim 11, wherein the fourth width is at least 90% of the third width.

19. The apparatus of claim 11, wherein the third width is about 1 to 2 mm.

20. The apparatus of claim 11, wherein the third width is less than the first width, and a surface area of a top surface of the annular rim is at least two times greater than a surface area of a top surface of the center post.

* * * * *